(12) United States Patent
Yamamoto et al.

(10) Patent No.: US 8,404,881 B2
(45) Date of Patent: Mar. 26, 2013

(54) WHITE PARTICLES FOR DISPLAY, PARTICLE DISPERSION FOR DISPLAY, DISPLAY MEDIUM AND DISPLAY DEVICE

(75) Inventors: Yasuo Yamamoto, Kanagawa (JP); Hiroaki Moriyama, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 248 days.

(21) Appl. No.: 12/552,851

(22) Filed: Sep. 2, 2009

(65) Prior Publication Data
US 2010/0225228 A1   Sep. 9, 2010

(30) Foreign Application Priority Data
Mar. 5, 2009   (JP) ................................. 2009-052028

(51) Int. Cl.
*C07F 7/08* (2006.01)
(52) U.S. Cl. ........ 556/430; 525/477; 524/268; 524/267; 524/730; 428/402
(58) Field of Classification Search ................ 556/430; 525/477; 524/267, 268, 730; 428/402
See application file for complete search history.

(56) References Cited

U.S. PATENT DOCUMENTS

| | | | | |
|---|---|---|---|---|
| 2,563,005 | A * | 8/1951 | Clark ............................ | 528/43 |
| 4,260,780 | A * | 4/1981 | West ............................ | 556/430 |
| 4,806,443 | A | 2/1989 | Yanus et al. | |
| 4,992,520 | A * | 2/1991 | Zeigler ......................... | 528/10 |
| 5,015,716 | A * | 5/1991 | Togashi et al. ................ | 528/15 |
| 5,017,654 | A * | 5/1991 | Togashi et al. ................ | 525/100 |
| 5,204,384 | A * | 4/1993 | Matsushita et al. ........... | 523/211 |
| 5,252,766 | A | 10/1993 | Sakakura et al. | |
| 5,374,758 | A * | 12/1994 | Mori et al. .................... | 556/430 |
| 5,403,943 | A * | 4/1995 | Tabei et al. ................... | 556/430 |
| 5,622,804 | A | 4/1997 | Matsuoka et al. | |
| 5,641,849 | A | 6/1997 | Nishida et al. | |
| 5,706,064 | A * | 1/1998 | Fukunaga et al. ............. | 349/43 |
| 5,723,250 | A | 3/1998 | Matsuoka et al. | |
| 5,863,684 | A | 1/1999 | Suzuki et al. | |
| 6,174,982 | B1 | 1/2001 | Nishida et al. | |
| 2005/0238975 | A1* | 10/2005 | Fujiki et al. ................... | 430/66 |
| 2008/0193769 | A1 | 8/2008 | Yanagisawa et al. | |
| 2009/0207476 | A1 | 8/2009 | Yanagisawa et al. | |

FOREIGN PATENT DOCUMENTS

| | | |
|---|---|---|
| JP | A-60-098431 | 6/1985 |
| JP | A-01-230638 | 9/1989 |
| JP | A-05-170913 | 7/1993 |
| JP | B2-05-170913 | 7/1993 |
| JP | A-07-017753 | 3/1995 |
| JP | B2-07-017753 | 3/1995 |
| JP | A-07-309953 | 11/1995 |
| JP | A-07-325434 | 12/1995 |
| JP | A-09-324053 | 12/1997 |
| JP | A-09-325507 | 12/1997 |
| JP | A-10-003177 | 1/1998 |
| JP | A-2000-273392 | 10/2000 |
| JP | A-2003-131420 | 5/2003 |
| JP | A-2003-192755 | 7/2003 |
| JP | A-2003-277507 | 10/2003 |
| JP | A-2004-043342 | 2/2004 |
| JP | A-2004-279732 | 10/2004 |
| JP | A-2005-036139 | 2/2005 |
| JP | A-2006-096985 | 4/2006 |
| JP | A-2007-231208 | 9/2007 |
| JP | A-2008-287102 | 11/2008 |
| WO | WO 98/29476 | 7/1998 |

OTHER PUBLICATIONS

Office Action issued in Japanese Application No. 2009-052028; Dated Oct. 19, 2010 (With Translation).

* cited by examiner

*Primary Examiner* — Margaret Moore
(74) *Attorney, Agent, or Firm* — Oliff & Berridge, PLC

(57) ABSTRACT

White particles for display including at least one of a chain or cyclic polysilane compound having a polysilane structure represented by the following Formula (I) or a halogen-substituted compound thereof:

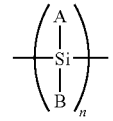

Formula (I)

wherein in Formula (I), A represents a phenyl group, B represents an alkyl group or a phenyl group, and n represents an integer of from 5 to 1000.

7 Claims, 5 Drawing Sheets

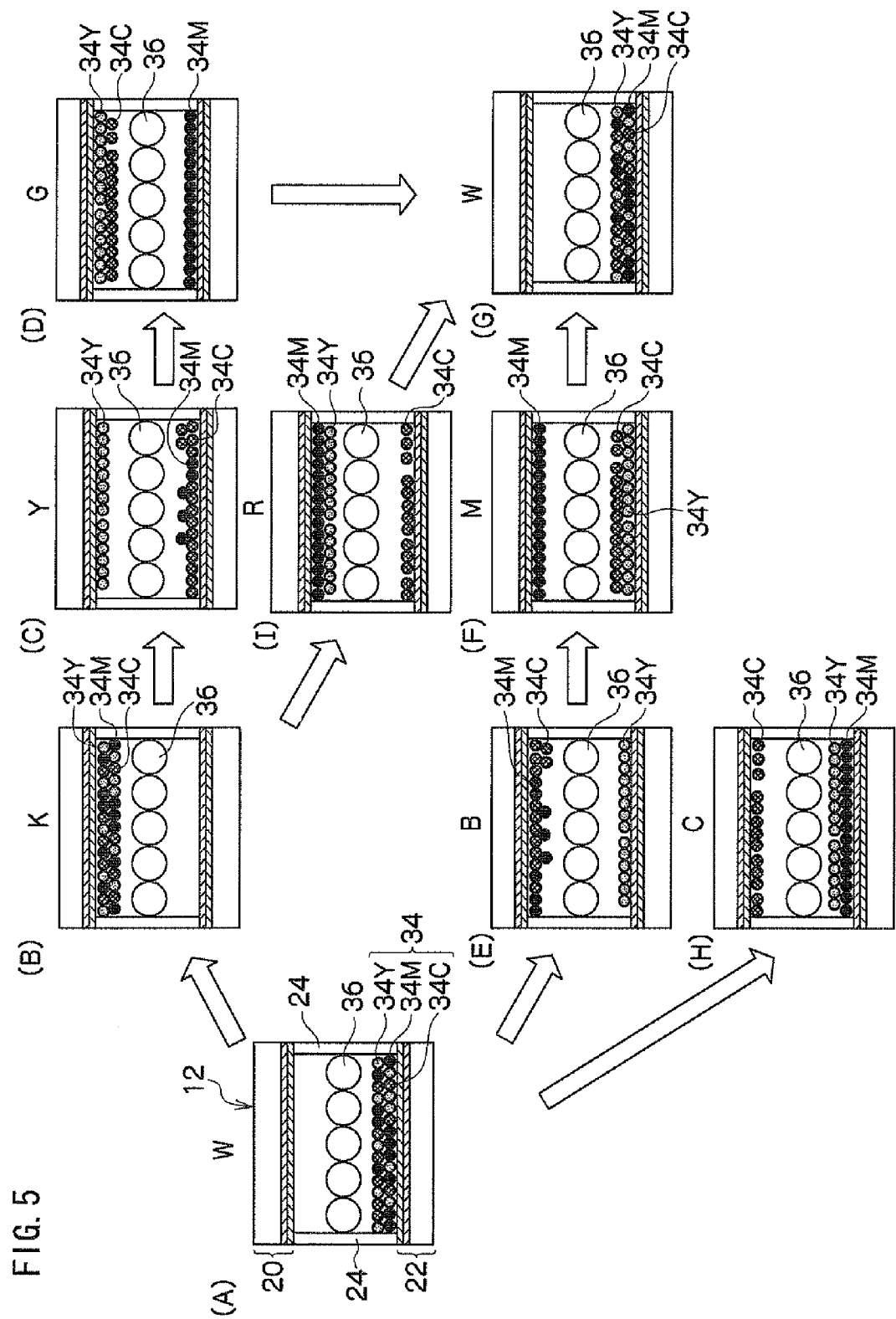

WHITE PARTICLES FOR DISPLAY, PARTICLE DISPERSION FOR DISPLAY, DISPLAY MEDIUM AND DISPLAY DEVICE

CROSS-REFERENCE TO RELATED APPLICATION

This application is based on and claims priority under 35 USC 119 from Japanese Patent Application No. 2009-052028 filed Mar. 5, 2009.

BACKGROUND

The invention relates to white particles for display, a particle dispersion for display, a display medium, and a display device.

RELATED ART

Conventionally, a display medium employing colored particles has been known as a re-writable display device. This display medium includes, for example, a pair of substrates and particles that are enclosed between the substrates such that the particles can move between the substrates in response to an electric field formed between the substrates.

SUMMARY

According to an aspect of the invention, there is provided white particles for display including at least one of a chain or cyclic polysilane compound having a polysilane structure represented by the following Formula (I) or a halogen-substituted compound thereof:

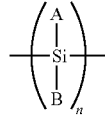

Formula (I)

wherein in Formula (I), A represents a phenyl group, B represents an alkyl group or a phenyl group, and n represents an integer of from 5 to 1000.

BRIEF DESCRIPTION OF THE DRAWINGS

Exemplary embodiments of the present invention will be described in detail based on the following figures, wherein:

FIG. 5 is a schematic view showing the relationship between the mode of voltage applied between the substrates of the display medium and the mode of movement of particles.

Figure 1:
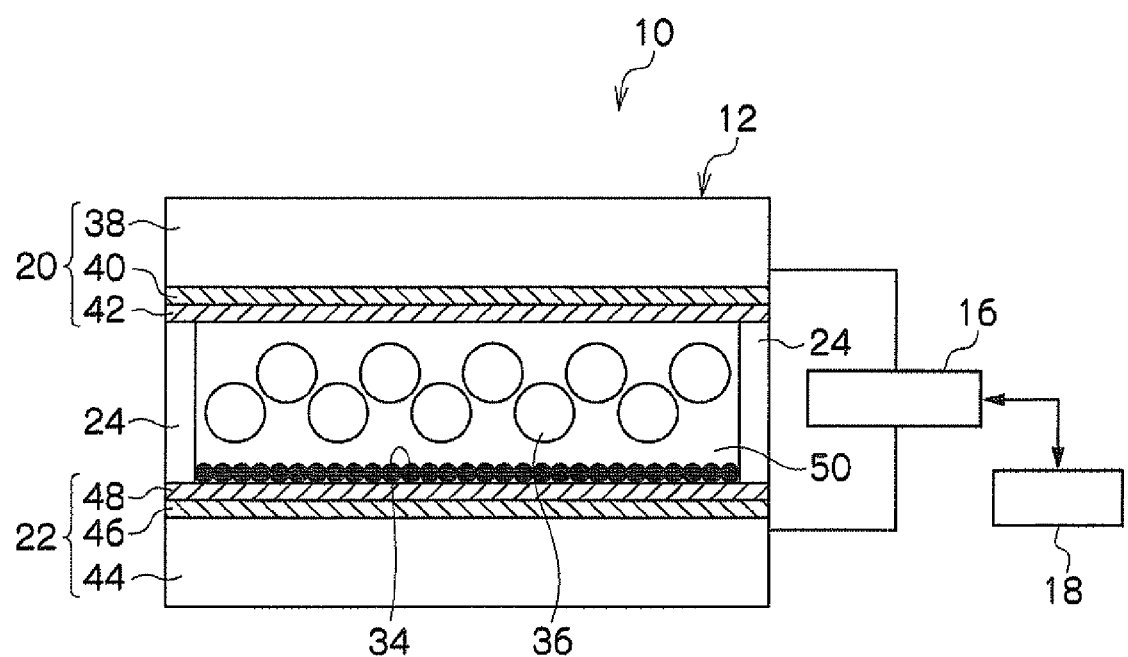
FIG. 1 is a schematic view of a display device according to a first exemplary embodiment of the invention.

DETAILED DESCRIPTION (White Particles for Display and Particle Dispersion for Display)

The white particles for display according to the invention include at least one of a linear or cyclic polysilane compound having a polysilane structure represented by the following Formula (I) or a halogen-substituted compound of the same.

Since the white particles for display according to the invention are a chain or cyclic polysilane compound having the following structure represented by Formula (I) or a halogen-substituted compound of the same (hereinafter, these compounds may be referred to as a specific polysilane compound) that exhibits a high refractive index (for example, 1.65 or more) and a small specific gravity (for example, 1.1 or less), sedimentation of particles may be suppressed while improving the whiteness. Further, when the white particles according to the invention are applied to a display medium, the dispersed state of particles having a high degree of whiteness may be easily maintained, thereby achieving display of a white color with a high degree of whiteness in a stable manner.

The white particles for display according to the invention may be formed from a powder of the specific polysilane compound itself, or may be resin particles with the specific polysilane compound dispersed or compounded therein, or fixed (attached) thereon. When the white particles for display according to the invention are resin particles, other components than the resin or the specific polysilane compound may also be included therein.

In the following, the components of the white particles for display according to the invention will be described.

The specific polysilane compound is a chain or cyclic polysilane compound having a polysilane structure represented by the following Formula (I) or a halogen-substituted compound of the same.

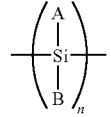

Formula (I)

In Formula (I), A represents a phenyl group, B represents an alkyl group or a phenyl group, and n represents an integer of from 5 to 1,000.

The alkyl group represented by B may be an alkyl group having 1 to 22 carbon atoms, preferably an alkyl group having 1 to 12 carbon atoms, more preferably an alkyl group having 1 to 6 carbon atoms. The alkyl group may be a straight-chain alkyl group or a branched alkyl group. Examples of the alkyl group include a methyl group, an ethyl group, a propyl group, an n-butyl group, a sec-butyl group, a hexyl group, an octyl group, an n-decyl group, an n-tetradecyl group, an n-hexadecyl group, an n-octadecyl group, a stearyl group, an isopropyl group, an isobutyl group, and an isopentyl group.

The specific polysilane compound may be a chain polysilane compound or a cyclic polysilane compound.

The chain polysilane compound preferably has a structure represented by the following Formula (I-1A). In Formula (I-1A), n represents an integer of from 100 to 1,000, preferably from 200 to 800, more preferably from 300 to 600. Examples of the terminal group of the chain polysilane compound include a hydroxyl group, a halogen atom, a methyl group, an ester group, an amino group, and a carboxyl group.

Formula (I-1A)

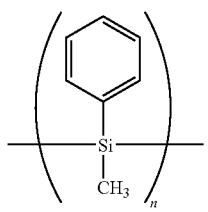

The cyclic polysilane compound preferably has a structure represented by the following Formula (I-2A). This cyclic polysilane compound has five of the structure represented by Formula (I), but a compound having six of the structure represented by Formula (I) is also preferred.

Formula (I-2A)

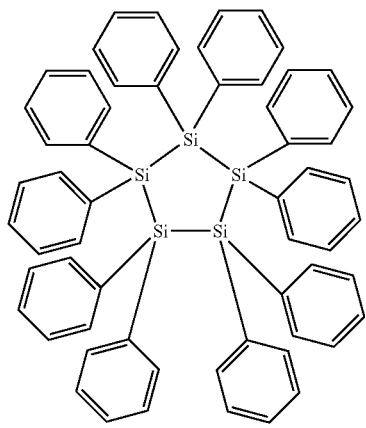

The specific polysilane compound may be a chain or cyclic halogen-substituted compound having a polysilane structure represented by Formula (I). The halogen-substituted compound refers to a polysilane compound in which a phenyl group of at least one of the polysilane structure represented by Formula (I) is substituted by a halogen atom (such as fluorine or chlorine). The halogen-substituted compound exhibits an improved refractive index as compared with the unsubstituted compound. Specific examples of the halogen-substituted polysilane compound include a chain polysilane compound represented by the following Formula (I-1B) or a cyclic polysilane compound represented by the following Formula (I-2B). In Formula (I-1B) and Formula (I-2B), R represents a halogen atom, and n has the same definitions as that of Formula (I-1A).

Formula (I-1B)

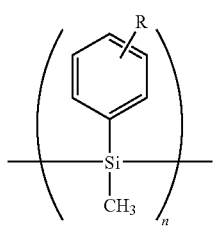

Formula (I-2B)

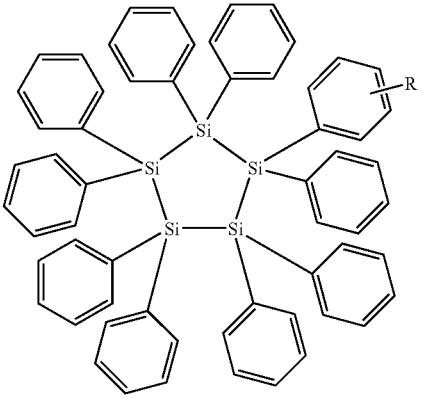

In the following, a method of synthesizing the specific polysilane compound will be described, taking the compound having a polysilane structure represented by Formula (I) as an example. The polysilane compound having the structure represented by Formula (I) may be synthesized according to a known method without being particularly limited. For example, the specific polysilane compound may be obtained by polymerizing a monomer that is obtained by reacting a silicon compound having a side chain A of the above polysilane with a Grignard reagent, which is a metal compound having a side chain B.

In order to regulate the molecular weight distribution (Mw/Mn) of the polysilane compound obtained by polymerizing the monomer as described above to 1.10 or less, it is preferred to recover the obtained polysilane compound by a precipitation-fractionation method. Here, the specific polysilane is a nonpolar polymer having no polar group in the molecule thereof. Therefore, the specific polysilane compound can be obtained by a precipitation-fractionation method, in which a poor solvent is gradually added to a solution of a good solvent in which the polysilane compound is dissolved, and then recovering a precipitation upon formation thereof.

The good solvent and the poor solvent used in the above process are not particularly limited, and may be appropriately selected depending on the structure of the polysilane compound. Examples of the good solvent include nonpolar solvents such as toluene, isooctane, and n-decane. Examples of the poor solvent include polar solvents such as isopropyl alcohol, ethanol, methanol, and water. Two or more kinds of poor solvent may be added to the good solvent including the polysilane compound. Namely, the weight average molecular weight of the polysilane compound obtained as a precipitate in the solvent differs depending on the polarity of the poor solvent. Therefore, the poor solvent is preferably selected so that a precipitation of polysilane compound having a desired weight average molecular weight can be obtained. In this precipitation-fractionation method, a large-scale production system is not necessary and a polysilane compound can be produced in large amounts in a simple and inexpensive process.

Further, by classifying the polysilane compound obtained in the above process for several times, different types of polysilane compound having different weight average molecular weights are obtained. Among these, several types of polysilane compound having different weight average molecular weights are selected and dissolved in a common solvent. The common solvent is not particularly limited as long as it is a good solvent, and may be appropriately selected according to the structure of the polysilane compound.

Other representative methods of synthesizing the specific polysilane compound include a method known as a Kipping method as described in Japanese Patent Application Laid-Open (JP-A) No. 9-324053, in which dialkyl dihalosilane or dihalotetraalkyl disilane in a toluene solvent is subjected to reductive coupling using an alkali metal such as metal sodium, while vigorously stirring the solvent at a temperature of 100° C. or more.

Other applicable methods include a method of anion-polymerizing a disilene masked with biphenyl or the like (Japanese Patent Application Laid-Open (JP-A) No. 1-230638); a method of performing ring-opening polymerization of a cyclic silane (JP-A No. 5-170913); a method of performing dehydrogenative condensation polymerization of a hydrosilane using a transition metal complex catalyst (JP-A No. 7-17753); a method of producing a polysilane by performing electrode reduction of a dihalosilane at room temperature or lower (JP-A No. 7-309953); a method of performing dehalogenation condensation polymerization of a halosilane using magnesium as a reduction agent (known as magnesium reduction method, see WO98/29476, JP-A No. 2003-277507 and JP-A No. 2005-36139).

In particular, the magnesium reduction method has advantages in that (1) a polysilane can be synthesized from an inexpensive raw material in a stable manner using a general-purpose chemical synthesis system, thereby enabling the synthesis in a safe and cost-effective manner; (2) inclusion of impurities such as sodium or substances that is insoluble to an organic solvent, which are not desirable for applications such as optical/electronic materials, does not occur; (3) a polysilane having a less variable molecular weight, a high degree of solubility with respect to an organic solvent and a high degree of transparency can be obtained; and (4) a polysilane can be obtained at high yield. Accordingly, the polysilane compound may be obtained by the magnesium reduction method. In this method, a polysilane compound is synthesized by polymerizing a halosilane under the presence of at least a magnesium metal component.

When the specific polysilane compound is dispersed or compounded in resin particles or fixed (attached) on the resin particles, the amount thereof is preferably from 3 to 99% by weight, more preferably from 10 to 70% by weight, with respect to the amount of resin that forms the resin particles.

The resin that forms the resin particles may be a thermoplastic resin or a thermosetting resin.

Examples of the thermoplastic resin include homopolymers or copolymers of styrenes (such as styrene and chlorostyrene), monoolefins (such as ethylene, propylene, butylene and isoprene), vinyl esters (such as vinyl acetate, vinyl propionate, vinyl benzoate and vinyl butyrate), α-methylene aliphatic monocarboxylates (such as methyl acrylate, ethyl acrylate, butyl acrylate, dodecyl acrylate, octyl acrylate, phenyl acrylate, methyl methacrylate, ethyl methacrylate, butyl methacrylate and dodecyl methacrylate), vinyl ethers (such as vinyl methyl ether, vinyl ethyl ether and vinyl butyl ether), and vinyl ketones (such as vinyl methyl ketone, vinyl hexyl ketone and vinyl isopropenyl ketone).

Examples of the thermosetting resins include crosslinked resins (such as a crosslinked copolymer including divinyl benzene as a main component and a crosslinked polymethyl methacrylate), phenol resins, urea resins, melamine resins, polyester resins and silicone resins.

The resin that forms the resin particles may be a polymer (resin) having a charging group. The polymer having a charging group refers to a polymer having a cationic group or an anionic group as a charging group. Examples of the cationic group include an amino group and a quaternary ammonium group (and a salt of these groups). These cationic groups positively charge the particles.

Examples of the anionic group include a phenol group, a carboxyl group, a carboxylate group, a sulfonic group, a sulfonate group, a phosphoric group, a phosphate group, and a tetraphenyl boron group (and a salt of these groups). These anionic groups negatively charge the particles.

The polymer having a charging group may be a homopolymer of a monomer having a charging group, or a copolymer of a monomer having a charging group and other monomer (a monomer having no charging group).

The monomer having a charging group may be a monomer having a cationic group (hereinafter, referred to as a cationic monomer) or a monomer having an anionic group (hereinafter, referred to as an anionic monomer). In the following, the description "(meth)acrylate" or the like refers to both acrylate and methacrylate.

Examples of the cationic monomer include (meth)acrylates having an aliphatic amino group, such as N,N-dimethylaminoethyl(meth)acrylate, N,N-diethylaminoethyl (meth)acrylate, N,N-dibutylaminoethyl(meth)acrylate, N,N-hydroxyethylaminoethyl (meth)acrylate, N-ethylaminoethyl (meth)acrylate, N-octyl-N-ethylaminoethyl (meth)acrylate, and N,N-dihexylaminoethyl(meth)acrylate; aromatic-substituted ethylene monomers having a nitrogen-containing group, such as dimethylaminostyrene, diethylaminostyrene, dimethylaminomethylstyrene and dioctylaminostyrene; nitrogen-containing vinyl ether monomers, such as vinyl-N-ethyl-N-phenylaminoethyl ether, vinyl-N-butyl-N-phenylaminoethyl ether, triethanolamine divinyl ether, vinyl diphenyl aminoethyl ether, N-vinyl hydroxyethyl benzamide, and m-aminophenyl vinyl ether; vinylamine; pyrroles such as N-vinyl pyrrole; pyrrolines such as N-vinyl-2-pyrroline and N-vinyl-3-pyrroline; pyrrolidines such as N-vinyl pyrrolidine, vinylpyrrolidine amino ether, and N-vinyl-2-pyrrolidone; imidazoles such as N-vinyl-2-methyl imidazole; imidazolines such as N-vinyl imidazoline, indoles such as N-vinyl indole, indolines such as N-vinyl indoline, carbazoles such as N-vinyl carbazole and 3,6-dibromo-N-vinyl carbazole, pyridines such as 2-vinyl pyridine, 4-vinyl pyridine and 2-methyl-5-vinyl pyridine, piperidines such as (meth)acrylic piperidine, N-vinyl piperidone and N-vinyl piperadine, quinolines such as 2-vinyl quinoline and 4-vinyl quinoline, pyrazoles such as N-vinyl pyrazole and N-vinyl pyrazoline, oxazoles such as 2-vinyl oxazole, and oxazines such as 4-vinyl oxazine and morpholinoethyl(meth)acrylate.

In view of versatility, the cationic monomer is preferably a (meth)acrylate having an aliphatic amino group such as N,N-dimethylaminoethyl(meth)acrylate and N,N-diethylaminoethyl(meth)acrylate. In particular, these monomers are preferably used in the form of a quaternary ammonium salt, before or after the polymerization. The quaternary ammonium salt may be obtained by allowing the monomer to react with an alkyl halide or a tosylate.

Examples of the anionic monomer include carboxylic acid monomers such as (meth)acrylic acid, crotonic acid, itaconic acid, maleic acid, fumaric acid, citraconic acid, anhydrides and monoalkyl esters of these monomers, and vinyl ethers having a carboxyl group such as carboxylethyl vinyl ether and carboxylpropyl vinyl ether;

sulfonic acid monomers such as styrene sulfonic acid, 2-acrylamide-2-methylpropane sulfonic acid, 3-sulfopropyl (meth)acrylic acid ester, bis-(3-sulfopropyl)-itaconic acid ester, a salt of these monomers, as well as other sulfonic acid monoesters such as 2-hydroxyethyl(meth)acrylic acid or a salt of these monomers; and phosphoric acid monomers such as vinyl phosphoric acid, vinyl phosphate, acid phosphoxyethyl(meth)acrylate, acid phosphoxypropyl(meth)acrylate, bis(methacryloyoxyethyl) phosphate, diphenyl-2-methacyloyloxyethyl phosphate, diphenyl-2-acryloyloxyethyl phosphate, dibutyl-2-methacryloyloxyethyl phosphate, dibutyl-2-acryloyloxyethyl phosphate, and dioctyl-2-(meth)acryloyloxyethyl phosphate.

The anionic monomer is preferably a monomer having (meth)acrylic acid or sulfonic acid, which is more preferably in the form of an ammonium salt before or after the polymerization. The ammonium salt may be obtained by allowing the monomer to react with a tertiary amine or a quaternary ammonium hydroxide.

Examples of the monomer having no charging group include a nonionic monomer such as (meth)acrylonitrile, alkyl(meth)acrylate, (meth)acrylamide, ethylene, propylene, butadiene, isoprene, isobutylene, N-dialkyl substituted (meth)acrylamide, styrene, styrene derivatives, vinyl carbazole, polyethylene glycol mono(meth)acrylate, vinyl chloride, vinylidene chloride, isoprene, butadiene, N-vinyl pyrrolidone, hydroxyethyl(meth)acrylate, and hydroxybutyl (meth)acrylate.

The copolymerization ratio of the monomer having a charging group and the monomer having no charging group may be determined depending on the desired charge amount of the particles, and is typically selected from the range of 1:100 to 100:1 (molar ratio, the monomer having a charging group:the monomer having no charging group).

The weight average molecular weight of the resin that forms the resin particles is preferably from 1,000 to 1,000,000, more preferably from 10,000 to 200,000.

Other materials that may be compounded in the resin particles include a charge control agent or a magnetic material. Examples of the charge control agent include known compounds used for electrophotographic toner materials, such as cetylpyridinium chloride, quaternary ammonium salts such as BONTRON P-51, BONTRON P-53, BONTRON E-84 and BONTRON E-81 (trade name, manufactured by Orient Chemical Industries, Co., Ltd.), salicylic metal complexes, phenol condensates, tetraphenyl compounds, metal oxide particles, or metal oxide particles having the surface treated with a coupling agent.

In the invention, a silicone polymer may be bound to (or applied on) the surface of the powder of the specific polysilane compound or resin particles having the aforementioned structure (hereinafter, referred to as white mother particles). The silicone polymer refers to a polymer including a silicone chain, preferably a polymer having a silicone chain (silicone graft chain) as a side chain, with respect to the main chain of the polymer.

One preferable example of the silicone polymer is a copolymer obtained from a silicone chain component and optionally at least one selected from an optional reactive component, a component having a charging group, and a component having no charging group. The raw material for these components (in particular, a silicone chain component) may be a monomer or a macromonomer. The macromonomer collectively refers to an oligomer (with a polymerization degree of 2 to about 300) or a polymer having a polymerizable functional group, and exhibits the characteristics of both of a polymer and a monomer.

Examples of the silicone chain component include a dimethyl silicone monomer having a (meth)acrylate group at one terminal end thereof, such as SILAPLANE FM-0711, FM-0721 and FM-0725 (trade name, manufactured by Chisso Corporation), X-22-174DX, X-22-2426 and X-22-2475 (trade name, manufactured by Shin-Etsu Chemical Co., Ltd.).

Examples of the reactive component include a glycidyl (meth)acrylate having an epoxy group, or an isocyanate monomer having an isocyanate group (such as KARENZ AOI and KARENZ MOI, trade name, Showa Denko K.K.)

Examples of the copolymerization component having a charging group or the copolymerization component having no charging group include the monomers having a charging group or the monomers having no charging group, such as those as mentioned above concerning the polymer having a charging group.

The silicone polymer may include a silicone chain component in an amount of from 3 to 60% by weight, preferably from 5 to 40% by weight with respect to the total amount of the polymer. When the amount of the silicone chain component is within the above range, stable dispersibility of the particles can be obtained while achieving other properties (such as imparting the charge polarity or controlling the charge amount).

Another example of the silicone polymer is a silicone compound having an epoxy group at one terminal end thereof (represented by the following Formula 1). Examples of the silicone compound having an epoxy group at one terminal end include X-22-173DX (trade name, manufactured by Shin-Etsu Chemical Con, Ltd.)

Formula 1

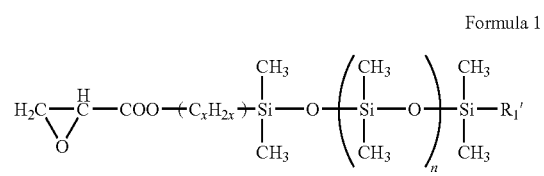

In Formula 1, $R_1'$ represents a hydrogen atom or an alkyl group having carbon atoms of 1 to 4, n represents a natural number of 1 to 1,000 for example, preferably 3 to 100, and x represents an integer of 1 to 3.

Yet another preferable example of the silicone polymer is a copolymer obtained from at least a dimethyl silicone monomer having a (meth)acrylate group at one terminal end thereof as represented by the following Formula 2, such as SILAPLANE FM-0711, FM-0721 and FM-0725 (trade name, manufactured by Chisso Corporation) and X-22-174DX, X-22-2426 and X-22-2475 (trade name, manufactured by Shin-Etsu Chemical Co., Ltd.), and a glycidyl(meth)acrylate or an isocyanate monomer, such as KARENZ AOI and KARENZ MOI (trade name, Showa Denko K.K.)

Formula 2

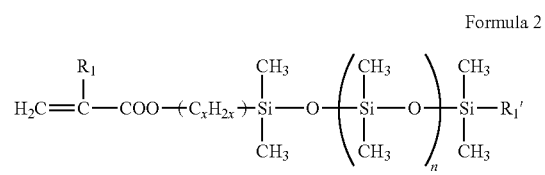

In Formula 2, $R_1$ represents a hydrogen atom or a methyl group, $R_1'$ represents a hydrogen atom or an alkyl group having carbon atoms of 1 to 4, n represents a natural number of 1 to 1,000 for example, preferably 3 to 100, and x represents an integer of 1 to 3.

The weight average molecular weight of the silicone polymer is preferably from 500 to 1,000,000, more preferably from 1,000 to 1,000,000.

The silicone polymer may be bonded to (or applied on) the white mother particles by a coacervation method.

The coacervation method includes dispersing the white mother particles as prepared by a known process (such as pulverization, coacervation, dispersion-polymerization or suspension-polymerization) in a first solvent in which the silicone polymer is dissolved, dropping a second solvent to the first solvent to emulsify the same, and then removing the first solvent and allowing the silicone polymer to precipitate on the surface of white mother particles and to react so as to be bonded to or applied on the surface of the white mother particles.

Examples of the first solvent include isopropyl alcohol (IPA), methanol, ethanol, butanol, tetrahydrofuran, ethyl acetate, and butyl acetate. Among these, isopropyl alcohol (IPA) is preferable since it can impart the particles stable dispersibility and charging properties. The second solvent is preferably a silicone oil.

The method of bonding or applying the silicone polymer to the white mother particles is not particularly limited to the above process.

The white particles for display according to the invention may have a volume average particle size of from 0.1 to 10 μm, preferably from 0.2 to 5 μm, more preferably from 0.3 to 1 μm.

When the volume average particle size to be measured is 2 μm or more, the measurement is conducted with a COULTER COUNTER TA-II (trade name, manufactured by Beckman Coulter, Inc.) using ISOTON-II (trade name, manufactured by Beckman Coulter, Inc.) as an electrolyte.

The measurement can be conducted by a method including adding 0.5 to 50 mg of a sample to 2 ml of an aqueous solution including a surfactant as a dispersant, preferably 0.5% of sodium alkylbenzene sulfonate, and adding the same to 100 to 150 ml of the aforementioned electrolyte; subjecting this electrolyte in which the sample is suspended to a dispersion treatment for 1 minute using an ultrasonic disperser; and then measuring the particle size distribution of the particles having a particle size of 2.0 to 60 μm using the COULTER COUNTER TA-II with an aperture having a diameter of 100 μm. The number of particles for measurement is 50,000.

Based on the particle size distribution as measured above, an accumulation distribution is delineated from the smaller size side, in each of volume and number with respect to the divided particle size range (channel). The particle size at which the volume accumulation is 16% is determined as D16v, and the particle size at which the accumulated number is 16% is determined as D16p. Similarly, the particle size at which the volume accumulation is 50% is determined as D50v, and the particle size at which the accumulated number is 50% is determined as D50p. Further, the particle size at which the volume accumulation is 84% is determined as D84v, and the particle size at which the accumulated number is 84% is determined as D84p. The volume average particle size is D50v.

Using the above indicators, the volume average particle size distribution index (GSDv) is calculated by $(D84v/D16v)^{1/2}$; the number average particle size distribution index (GSDp) is calculated by $(D84p/D16p)^{1/2}$; and the number average particle size distribution index at the smaller size side (lower GSDp) is calculated by $\{(D50p)/(D16p)\}$.

When the volume average particle size to be measured is less than 2 μm, the measurement is conducted with a laser scattering particle size measurement device (trade name: LA-700, manufactured by Horiba, Ltd.) Specifically, a sample in the form of a dispersion with a solid content of 2 g is prepared and ion exchange water is added to the sample to give the total amount of 40 ml, and the sample is placed in a cell to give an appropriate concentration. After 2 minutes, when the concentration in the cell is stabilized, the measurement is conducted. The volume average particle size as measured at each channel is accumulated from the side of smaller particles size, and the particle size at which the accumulation is 50% is determined as the volume average particle size.

The amount of a powder such as an external agent is measured by adding 2 g of a sample in 50 ml of 0.5% aqueous solution of a surfactant, preferably sodium alkylbenzene sulfonate, dispersing the same using an ultrasonic disperser (1,000 Hz) for 2 minutes, and then conducting the measurement in accordance with the method as mentioned above.

The white particles for display according to the invention may be used as mobile particles that move in response to an electric field, or as non-mobile particles that do not move in response to an electric field. When the white particles for display according to the invention are used as mobile particles that move in response to an electric field, the particles are formed by using a polymer having a charging group as the resin that forms the particles, or by using a component having a charging group for the silicone polymer. On the other hand, when the white particles for display according to the invention are used as non-mobile particles that do not move in response to an electric field, the particles are formed by using a polymer having no charging group as the resin that forms the particles, or by using a component having no charging group for the silicone polymer. The charging group refers to a group having a tendency of being ionized by acid or base dissociation, and examples thereof include an amino group and a carboxyl group.

The particle dispersion for display that employs the white particles according to the invention includes the white particles for display according to the invention, and a dispersing medium in which the particles are dispersed. The particle dispersion for display according to the invention may include other particles for display (color particles). As necessary, the particle dispersion may further include an acid, an alkali, a salt, a dispersant, a dispersion stabilizer, a stabilizer for antioxidization or UV absorption, an antibacterial agent, an antiseptic agent, or the like.

The dispersing medium may be any material that can be used for a display medium, but when the aforementioned silicone polymer is bonded to or coated on the surface of the white particles, a silicone oil is preferably used.

Examples of the charge control agent include an ionic or nonionic surfactant, a block or graft copolymer having a lipophilic portion and a hydrophilic portion, a compound having a polymeric skeleton of a cyclic, stellate, or dendritic structure, a salicyclic metal complex, a catechol metal complex, a metal-containing bisazo dye, a tetraphenyl borate derivative, and a copolymer of a polymerizable macromer (such as SILAPLANE, trade name, manufactured by Chisso Corporation) and an anionic monomer or a cationic polymer.

Examples of the nonionic surfactant include polyoxyethylene nonyl phenyl ether, polyoxyethylene octyl phenyl ether, polyoxyethylene dodecyl phenyl ether, polyoxyethylene alkyl ether, polyoxyethylene fatty acid ester, sorbitan fatty acid ester, polyoxyethylene sorbitan fatty acid ester, and fatty acid alkylol amide.

Examples of the anionic surfactant include alkyl benzene sulfonate, alkyl phenyl sulfonate, alkyl naphthalene sulfonate, higher fatty acid salt, a sulfate of higher fatty acid ester, and a sulfonate of higher fatty acid ester.

Examples of the cationic surfactant include a primary to tertiary amine salt, or a quaternary ammonium salt.

The charge control agents is preferably included in an amount of from 0.01 to 20% by weight, particularly preferably from 0.05 to 10% by weight, with respect to the solid content of the particles.

The particles for display and the particle dispersion for display according to the invention are applicable to an electrophoresis display medium, a liquid toner for use in an electrophotographic system employing a liquid developing system, or the like.

(Display Medium and Display Device)

In the following, exemplary embodiments of the display medium and the display device will be described.

First Exemplary Embodiment

Figure 2A:
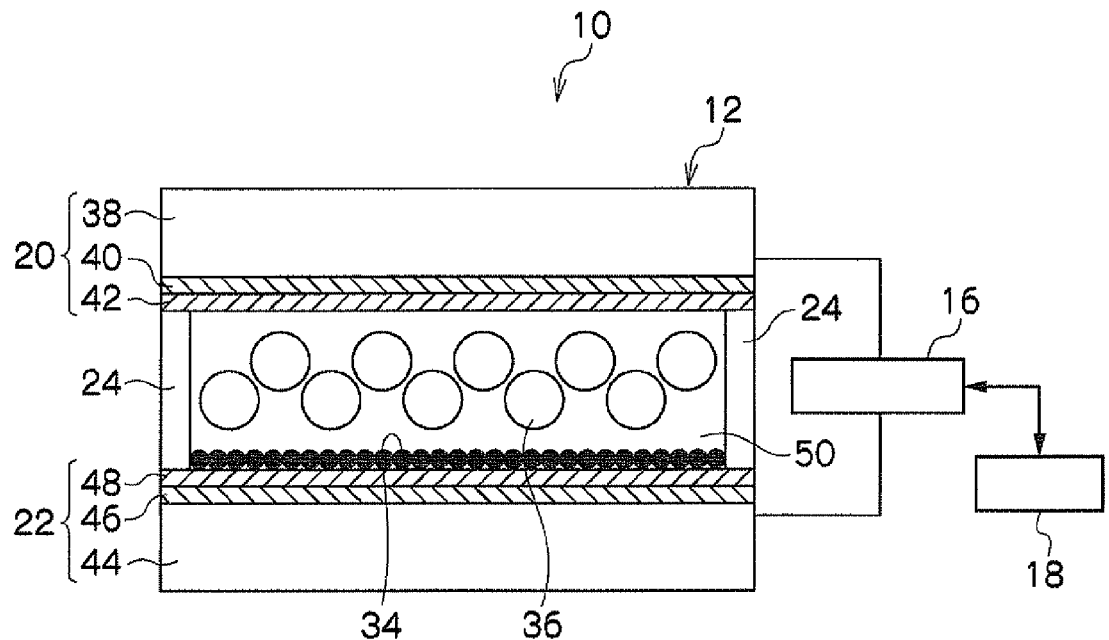
FIGS. 2A and 2B are schematic views showing how the particles move upon application of a voltage between the substrate of the display device according to the first exemplary embodiment of the invention.
Figure 2B:
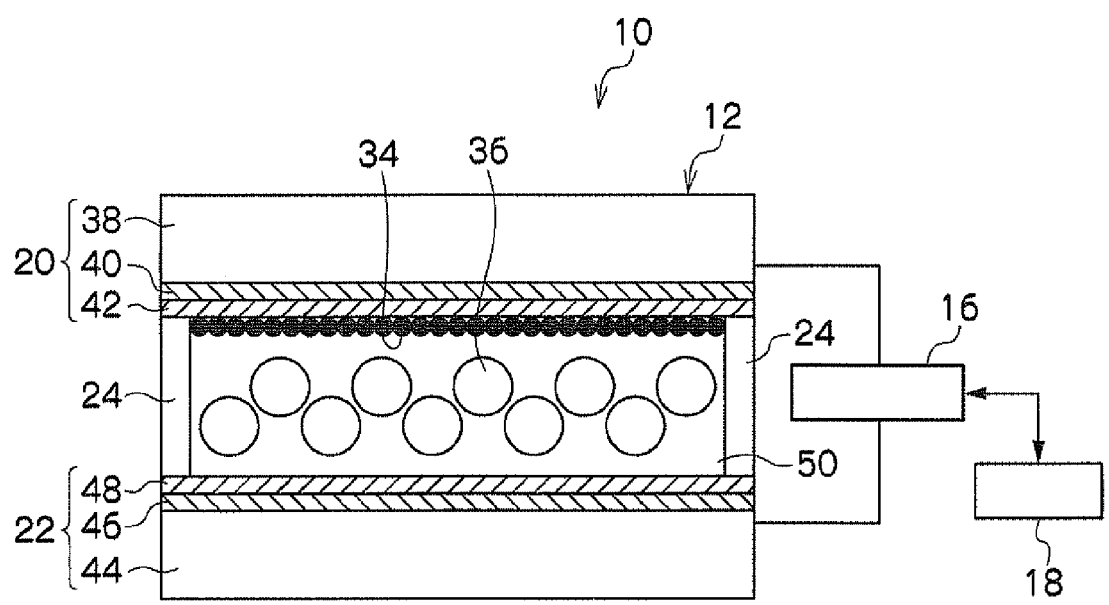

FIG. 1 is a schematic view of a display device according to the first exemplary embodiment. FIGS. 2A and 2B are schematic views showing how the particles move upon application of a voltage between the substrates of the display device according to the first exemplary embodiment of the invention.

Display device 10 according to the first exemplary embodiment employs color particles having a color other than white as mobile particles 34, and the white particles for display according to the invention as reflective particles 36. It is also possible to employ the white particles for display according to the invention as mobile particles 34.

Display device 10 includes, as shown in FIG. 1, a display medium 12, a voltage application unit 16 that applies a voltage to display medium 12, and a control unit 18.

Display medium 12 includes a display substrate 20 that displays an image; a rear substrate 22 that is positioned opposite to display substrate 20 with a space; spacers 24 that maintain the substrates to be positioned with a specified space and divide the space between the substrates into plural cells; mobile particles 34 included in each cell; and reflective particles 36 having a different optical reflection property than that of mobile particles 34.

The cell as mentioned above refers to a space surrounded by display substrate 20, rear substrate 22, and spacers 24. A dispersing medium 50 is included in the cell. Mobile particles 34 consisting of plural kinds of particles are dispersed in dispersing medium 50, and move between display substrate 20 and rear substrate 22 through the gaps among reflective particles 36 in response to an electric field formed in the cell.

In this exemplary embodiment, mobile particles 34 included in each cell are described as having a single specific color and have been previously treated to be either positively or negatively charged.

It is also possible to configure display medium 12 so that display can be performed in each pixel, by providing spacers 24 to form a cell so as to correspond to each pixel of an image to be displayed.

For the purpose of simplification, this exemplary embodiment will be described referring to a drawing that shows only a single cell. In the following, details of each component will be described.

Display substrate 20 includes, on a support 38, a front electrode 40 and a surface layer 42 in this order. Rear substrate 22 includes, on a support 44, a rear electrode 46 and a surface layer 48 in this order.

Only display substrate 20, or both display substrate 20 and rear substrate 22 are transparent. In this exemplary embodiment, being transparent refers to having a transmittance with respect to visible rays of 60% or more.

Materials for support 38 and support 44 include glass and plastics such as polyethylene terephthalate resin, polycarbonate resin, acrylic resin, polyimide resin, polyester resin, epoxy resin, and polyether sulfone resin.

Materials for front electrode 40 and rear electrode 46 includes oxides of indium, tin, cadmium, antimony or the like, composite oxides such as ITO, metals such as gold, silver, copper or nickel, and organic materials such as polypyrrole or polythiophene. Front electrode 40 and rear electrode 46 may be formed from a material such as those to a single film, a mixed film or a composite film, by a method of evaporation, sputtering, coating or the like. The thickness of front electrode 40 and rear electrode 46 is typically from 100 to 2,000 angstroms, when these electrodes are formed by evaporation or sputtering. Front electrode 40 and rear electrode 46 may be formed in a desired patterned manner by a known method such as etching that is performed to form conventional liquid crystal displays or printed boards. For example, front electrode 40 and rear electrode 46 may be formed in a matrix pattern or a striped pattern that enables passive matrix driving.

Front electrode 40 may be embedded in support 38, or rear electrode 46 may be embedded in support 44. In this case, the material for supports 38 and 44 is selected in accordance with the composition of each kind of mobile particles 34.

Front electrode 40 and rear electrode 46 may be separated from display substrate 20 and rear substrate 22, and positioned outside display medium 12.

In the above description, both display substrate 20 and rear substrate 22 are provided with an electrode (front electrode 40 and rear electrode 46). However, it is also possible to provide an electrode only to one substrate for performing active matrix driving.

In order to enable active matrix driving, a thin film transistor (TFT) may be provided to support 38 and support 44 at each pixel. The TFT is preferably formed on rear substrate 22 rather than on display substrate 20, since formation of a multilayer wiring or packaging may be readily conducted.

When display medium 12 is driven by the passive matrix system, configuration of display device 10 including display medium 12 can be simplified. When display medium 12 is driven by the active matrix system, the display speed can be increased as compared with the passive matrix system.

When front electrode 40 and rear electrode 46 are formed on support 38 and support 44, respectively, dielectric films as surface layers 42 and 48 are optionally formed on front electrode 40 and rear electrode 46, respectively, in order to prevent breakage of the electrodes or leakage between the electrodes that causes fixation of mobile particles 34.

Materials for surface layers 42 and 48 include polycarbonate, polyester, polystyrene, polyimide, epoxy, polyisocyanate, polyamide, polyvinyl alcohol, polybutadiene, polymethylmethacrylate, copolymerized nylon, UV-cured acrylic resin, and fluorocarbon resin.

Other than the aforementioned insulating materials, an insulating material in which a charge transporting substance is included may also be used. Inclusion of a charge transporting substance may provide such effects as improving the charging properties of the particles by charge injection, allowing the charges to leak from the particles when the amount of the charges is exceedingly increased, so as to stabilize the amount of charges to the particles.

Examples of the charge transporting substance include hole transporting substances such as hydrazone compounds, stilbene compounds, pyrazoline compounds, and arylamine compounds; and electron transporting substances such as fluorenone compounds, diphenoquinone compounds, pyrane compounds, and zinc oxide.

A self-supporting resin having a charge transporting property may also be used. Specific examples thereof include polyvinyl carbazole, and a polycarbonate obtained by polymerizing a specific hydroxyarylamine and bischloroformate, as described in the U.S. Pat. No. 4,806,443.

Since the dielectric film may affect the charging properties or fluidity of the particles, the material thereof is selected in accordance with the composition of the particles, or the like. Since display substrate 20 needs to be transparent, the surface layer of display substrate 20 is preferably formed from a transparent material.

Spacers 24 that maintain a space between display substrate 20 and rear substrate 22 are formed so as not to impair the transparency of display substrate 20, and are formed from thermoplastic resin, thermosetting resin, electron beam-curing resin, photo-curing resin, rubber, metal, or the like.

Spacers 24 may be formed in an integrated manner with either display substrate 20 or rear substrate 22. In this case, spacers 24 may be formed by subjecting support 38 or support 44 to an etching treatment, laser treatment, pressing treatment using a predetermined pattern, or printing treatment.

In this case, spacers 24 are formed on either side of display substrate 20 or rear substrate 22, or on both sides.

Spacers 24 may have a color or colorless, but is preferably colorless and transparent so as not to affect the image displayed on display medium 12. In this case, for example, spacers 24 are formed from a transparent polystyrene resin, polyester resin, or acrylic resin.

When spacers 24 are in a particulate form, spacers 24 may also be formed from glass particles, as well as particles of a transparent polystyrene resin, polyester resin, or acrylic resin.

Being transparent here refers to having a transmittance of 60% or more with respect to visible rays.

Mobile particles 34 included in display medium 12 may be dispersed in a polymeric resin as dispersing medium 50. This polymeric resin may be a polymeric gel or a polymeric polymer.

Examples of the polymeric gel include most types of synthesis polymeric gel, and polymeric gels derived from a natural polymer such as agarose, agaropectin, amylose, sodium alginate, propylene glycol alginate, isolichenan, insulin, ethyl cellulose, ethylhydroxy ethyl cellulose, curdlan, casein, carrageenan, carboxymethyl cellulose, carboxymethyl starch, callose, agar, chitin, chitosan, silk fibroin, guar gum, quince seed, crown-gall polysaccharide, glycogen, glucomannan, keratan sulfate, keratin protein, collagen, cellulose acetate, gellan gum, schizophyllan, gelatin, ivory palm mannan, tunicin, dextran, dermatan sulfate, starch, tragacanth gum, nigeran, hyaluronic acid, hydroxyethyl cellulose, hydroxypropyl cellulose, pusturan, funoran, decomposed xyloglucan, pectin, porphyran, methyl cellulose, methyl starch, laminaran, lichenan, lentinan, and locust beam gum.

Further examples include polymers including a functional group of alcohol, ketone, ether, ester or amide in the repeating unit, such as polyvinyl alcohol, poly(meth)acrylamide, derivatives thereof, polyvinyl pyrrolidone, polyethylene oxide, or copolymers including these polymers.

Among these, gelatin, polyvinyl alcohol and poly(meth)acrylamide are preferably used in view of production stability and electrophoretic properties.

The aforementioned polymeric resin is preferably used as dispersing medium 50 together with the aforementioned insulating material.

Mobile particles 34 included in each cell and consisting of plural kinds of particles are dispersed in dispersing medium 50, and move between display substrate 20 and rear substrate 22 in response to the strength of an electric field formed in the cell.

Particles that constitute mobile particles 34 may be particles of an insulating metal oxide such as glass, alumina or titanium oxide, particles of thermoplastic resin or thermosetting resin, resin particles with a colorant fixed on the surface thereof particles of thermoplastic resin or thermosetting resin including an insulating colorant therein, particles of metal colloid having a plasmon coloring function, or the like.

Examples of the thermoplastic resin for the mobile particles include homopolymers or copolymers of styrenes (such as styrene and chlorostyrene), mono-olefins (such as ethylene, propylene, butylene and isoprene), vinyl esters (such as vinyl acetate, vinyl propionate, vinyl benzoate and vinyl butyrate), α-methylene aliphatic monocarboxylates (such as methyl acrylate, ethyl acrylate, butyl acrylate, dodecyl acrylate, octyl acrylate, phenyl acrylate, methyl methacrylate, ethyl methacrylate, butyl methacrylate and dodecyl methacrylate), vinyl ethers (such as vinyl methyl ether, vinyl ethyl ether and vinyl butyl ether), and vinyl ketones (such as vinyl methyl ketone, vinyl hexyl ketone and vinyl isopropenyl ketone).

Examples of the thermosetting resins for the mobile particles include crosslinked resins (such as a crosslinked copolymer including divinyl benzene as a main component and a crosslinked polymethyl methacrylate), phenol resins, urea resins, melamine resins, polyester resins and silicone resins. Particularly representative binder resins include polystyrene, styrene-alkyl acrylate copolymer, styrene-alkyl methacrylate copolymer, styrene-acrylonitrile copolymer, styrene-butadiene copolymer, styrene-maleic anhydride copolymer, polyethylene, polypropylene, polyester, polyurethane, epoxy resin, silicone resin, polyamide, modified rosin, and paraffin wax.

Examples of the colorant include organic or inorganic pigments or oil-soluble dye. Examples of known colorants include magnetic powder of magnetite, ferrite or the like, carbon black, titanium oxide, magnesium oxide, zinc oxide, phthalocyanine copper cyano colorant, azo yellow colorant, azo magenta colorant, quinacridone magenta colorant, red colorant, green colorant and blue colorant. Specific example thereof include aniline blue, calco oil blue, chrome yellow, ultramarine blue, DuPont oil red, quinoline yellow, methylene blue chloride, phthalocyanine blue, malachite green oxalate, lamp black, rose bengal, C.I. pigment red 48:1, C.I. pigment red 122, C.I. pigment red 57:1, C.I. pigment yellow 97, C.I. pigment blue 15:1, C.I. pigment blue 15:3. These colorants may be used alone or in combination.

As necessary, a charge control agent may be mixed in the resin for the mobile particles. Known charge control agents for use in electrophotographic toner materials are applicable, and examples thereof include cetylpyridinium chloride, quaternary ammonium salts such as BONTRON P-51, BONTRON P-53, BONTRON E-84 and BONTRON E-81 (trade name, manufactured by Orient Chemical Industries, Co., Ltd.), salicylic metal complexes, phenol condensates, tetraphenyl compounds, metal oxide particles, and metal oxide particles having the surface treated with a coupling agent of various kinds.

As necessary, a magnetic material may be mixed in the mobile particles, or applied on the surface thereof. The magnetic material may be an organic or inorganic magnetic material that may have an optional coating of a colorant. A transparent magnetic material, especially a transparent organic magnetic material is preferred since it does not inhibit coloring of the colored pigment, and has a specific gravity that is less than that of the organic magnetic material.

A colored magnetic powder, such as the small colored magnetic powder as disclosed in JP-A No. 2003-131420, may be used as the magnetic material. For example, a magnetic powder including a core magnetic particle and a color layer formed on the core magnetic particles may be used. In this case, the color layer may be selected so as to color the magnetic powder with a pigment or the like in an opaque manner, but a thin film that exhibits a color by light interference is preferred. This thin film is formed from a colorless material such as $SiO_2$ or $TiO_2$ to a thickness equivalent to a wavelength of light, and reflects light in a selective manner due to light interference inside the thin film.

As necessary, an external additive may be attached to the surface of the mobile particles. The color of the external additive is preferably transparent so as not to affect the color of the mobile particles.

Materials for the external additive include particles of a metal oxide such as silicon oxide (silica), titanium oxide or alumina. The mobile particles may be surface-treated with a coupling agent or silicone oil, in order to adjust the charging property, fluidity or environment dependency of the mobile particles.

Examples of the coupling agent include positively charged ones such as aminosilane coupling agents, aminotitanium coupling agents and nitrile coupling agents, and negatively charged ones that do not include a nitrogen atom (consisting of atoms other than a nitrogen atom) such as silane coupling agent, titanium coupling agent, epoxysilane coupling agent, and acrylsilane coupling agent.

Examples of the silicone oil include positively charged ones such as amino-modified silicone oil, and negatively charged ones such as dimethyl silicone oil, alyl-modified silicone oil, α-methylsulfone-modified silicone oil, methylphenyl silicone oil, chlorophenyl silicone oil, and fluorine-modified silicone oil.

These coupling agents or silicone oils may be selected depending on the desired resistivity of the external additive.

Among the above external additives, hydrophobic silica and hydrophobic titanium oxide that are well known in the art are preferred, and a titanium compound obtained by allowing $TiO(OH)_2$ to react with a silane compound such as a silane coupling agent, as described in JP-A No. 10-3177, is particularly preferred. Any of chlorosilanes, alkoxy silanes, silazanes, or speciality silylation reagents may be used as the silane compound. This titanium compound may be produced by allowing $TiO(OH)_2$ produced in a wet process to react with a silane compound or a silicone oil, and then drying the reactant. Since this process does not include sintering at a temperature of as high as several hundreds, no strong bond is formed among the Ti atoms and no aggregation occurs. Therefore, the mobile particles are in the form of primary particles. Further, since $TiO(OH)_2$ is directly allowed to react with a silane compound or silicone oil, it is possible to control the charging properties by adjusting the amount of silane compound or silicone oil used for the treatment and even more improved charging properties can be achieved as compared with those of conventional titanium oxide.

The volume average particle size of the external additive is not particularly limited, but is typically from 5 nm to 100 nm, more preferably from 10 nm to 50 nm.

The compounding ratio of the external additive and the mobile particles may be determined depending on the size of the mobile particles and the external additive. When the amount of the external additive is too large, part of the external additive may be detached from the surface of mobile particles and attach to the surface of other mobile particles, thereby failing to obtain desired charging properties. Typically, the amount of the external additive may be from 0.01 to 3 parts by weight, preferably from 0.05 to 1 part by weight, with respect to 100 parts by weight of the mobile particles.

The external additive may be added to only one kind of the mobile particles, or may be added to two or more kinds, or all kinds of the mobile particles. The addition of the external additive to the surface of the mobile particles is preferably conducted by striking the external additive in the surface of the mobile particles with impact strength, or heating the surface of the mobile particles, so that the external additive is tightly fixed on the surface of the mobile particles. In this way, it is possible to inhibit external additive from being detached from the mobile particles and forming an aggregate of the external additive having different polarities that is hard to be dissociated by an electric field, thereby suppressing degradation of an image.

In this exemplary embodiment, mobile particles 34 will be described as having previously adjusted characteristics that contribute to the migration of mobile particles 34 in response to an electric field, such as the average charge amount or electrostatic amount, so that mobile particles 34 can move between display substrate 20 and rear substrate 22 in response to an electric field formed between these substrates.

The adjustment of average charge amount of each mobile particle of mobile particles 34 may be performed, specifically, by adjusting the type or amount of charge control agent to be compounded in the resin as mentioned above, the type or amount of polymer chain to be bound to the surface of the mobile particles, the type or amount of external additive to be added or embedded into the surface of the mobile particles, the type or amount of the surfactant, polymer chain or coupling agent to be applied to the surface of the mobile particles, or the specific surface area of the mobile particles (such as the volume average particle size or the shape factor).

The production of mobile particles 34 may be performed by any known method.

For example, as described in JP-A 7-325434, mobile particles 34 may be produced by measuring a resin, a pigment and a charge controlling agent at a specific mixing ratio, melting the resin by heating and adding the pigment thereto and mixing and dispersing the same, cooling and pulverizing the same using a jet mill, a hammer mill or a turbo mill to prepare the mobile particles, and then dispersing the obtained mobile particles in a dispersing medium.

Further, mobile particles 34 may be produced by preparing the mobile particles including the charge control agent inside thereof by a polymerization method such as suspension-polymerization, emulsification-polymerization or dispersion-polymerization, or an aggregation method such as coacervation, melt dispersion or emulsion-aggregation, and then the obtained mobile particles in a dispersing medium to prepare a dispersing medium including the mobile particles.

Moreover, there is a method of using an appropriate device that performs dispersion, mixing and kneading of the resin, colorant, charge control agent and/or dispersing medium at a temperature that is lower than the point of decomposition of the resin, colorant, charge control agent and/or dispersing medium, at which temperature the resin can plasticize and the dispersing medium does not boil. Specifically, the mobile particles can be obtained by mixing and heating to melt the pigment, resin and charge control agent in the dispersing medium using a planetary mixer or a kneader, cooling the mixture while stirring using the temperature dependency of the solvent solubility of the resin, and then allowing the mixture to coagulate/precipitate to form the mobile particles.

Additionally, there is a method of producing the mobile particles including placing the aforementioned raw materials in an appropriate container equipped with particulate media for dispersing and kneading, such as an attritor or a heated vibrating mill such as a ball mill, and then dispersing and kneading the content of the container at an appropriate temperature range, such as from 80 to 160° C. Preferred examples of the material for the particulate media include steels such as stainless steel or carbon steel, alumina, zirconia or silica. When producing the mobile particles by this method, the raw materials that have been previously made into a fluid state are further dispersed by the particulate media in the container, and the resin including the colorant is allowed to precipitate from the dispersing medium by cooling the dispersing medium. The particulate media maintain the state of motion during the cooling and after the cooling, and reduce the size of particles by generating shearing force or impact strength.

The content of mobile particles 34 (weight %) with respect to the total weight of the content of the cell is not particularly limited as long as the desired color hue can be obtained. It is effective for display medium 12 to adjust the content of mobile particles 34 by adjusting the thickness of the cell (i.e., the distance between display substrate 20 and rear substrate 22). Namely, in order to achieve the desired color hue, the content of mobile particles 34 can be reduced (or increased) by increasing (or reducing) the thickness of the cell. The content of mobile particles 34 is typically from 0.01 to 50% by weight.

Reflective particles 36 are particles that are not charged and include particles having different optical reflection characteristics than that of mobile particles 34, and function as a reflective member that displays a different color from that of mobile particles 34. Further, reflective particle 36 function as a spacer which allows mobile particles 34 to move through the space between display substrate 20 and rear substrate 22 without inhibiting the movement of mobile particles 34. Namely, each particle of mobile particles 34 moves through gaps among reflective particles 36 from the side of rear substrate 22 toward the side of display substrate 20, or from the side of display substrate 20 toward the side of rear substrate 22. The color of reflective particles 36 may have, for example, a black color for the background, other than the white color. Further, reflective particles 36 may be particles that are charged and move in response to an electric field.

When reflective particles 36 have a color other than white, reflective particles may be resin particles including a colorant such as a pigment or dye having a desired color. The pigment or dye may be those typically used in printing inks or color toners, such as those of RGB or YMC colors.

Reflective particles 36 may be included between the substrates by an inkjet method or the like. Further, reflective particles 36 may be fixed. In this case, for example, reflective particles 36 after being included between the substrates are heated (and pressed if necessary) to melt the surface of the particles, such that the gaps between the particles are maintained. Reflective particles 36 may be filled between the substrates, or may be suspended in a dispersing medium between the substrates.

The content of reflective particles 36 (% by weight) with respect to the total weight of the content of the cell is not particularly limited as long as the desired color hue can be obtained. It is effective for display medium 12 to adjust the content of reflective particles 36 by adjusting the thickness of the cell (i.e., the distance between display substrate 20 and rear substrate 22). Namely, in order to achieve the desired color hue, the content of reflective particles 36 can be reduced (or increased) by increasing (or reducing) the thickness of the cell. The content of reflective particles 36 is typically from 0.01 to 70% by weight.

The size of the cell in display medium 12 has a close relationship with the definition of display medium 12, and display medium 12 that can display an image with a higher definition can be produced by reducing the size of the cell. The cell typically has a length in a plane direction of display substrate 20 of from 10 μm to about 1 mm.

Display substrate 20 and rear substrate 22 can be fixed to each other via spacers 24 using a combination of bolt and nut, a clamp, a clip, a flame for fixing the substrates, or the like. Alternatively, the substrates may be fixed to each other using an adhesive, or by performing hot-melting, ultrasonic bonding, or the like.

Display medium 12 having the aforementioned structure is applicable to media that can record an image or re-writing an image, such as bulletin boards, circulars, electronic black boards, advertisements, billboards, flash signals, electronic paper, electronic newspapers, electronic books, and document sheets for use in both copiers and printers.

As mentioned above, display device according to this exemplary embodiment includes display medium 12, voltage application unit 16 that applies a voltage to display medium 12, and control unit 18 (see FIG. 1).

Voltage application unit 16 is electrically connected to front electrode 40 and rear electrode 46. In the following, both of front electrode 40 and rear electrode 46 are described as being electrically connected to voltage application 16. However, it is also possible that one of these electrodes is grounded while the other is electrically connected to voltage application 16.

Voltage application unit 16 is connected to control unit 18 such that voltage application unit 16 can give or receive signals.

Control unit 18 may be a microcomputer including a CPU (central processing unit) that controls operation of the whole device, a RAM (random access memory) that temporarily records data of various kinds, and a ROM (read only memory) in which programs of various kinds, such as control program for controlling the whole device, are recorded.

Voltage application unit 16 applies a voltage to front electrode 40 and rear electrode 46 in accordance with instructions from control unit 18.

In the following, the behavior of display device 10 will be described in accordance with the operation of control unit 18.

Mobile particles 34 included in display medium 12 are described as black and negatively charged. Dispersion medium 50 is described as transparent, and reflective particles 36 are described as white. Namely, in this exemplary embodiment, display medium 12 displays a black color or a white color depending on the movement of mobile particles 34.

First, an initial operation signal is output to voltage application unit 16. This signal indicates application of a voltage for a specified time period, such that front electrode 40 serves as a negative electrode and rear electrode 46 serves as a positive electrode. When a voltage that is negative and greater than a threshold voltage at which changes in the concentration of particles stops is applied between the substrates, mobile particles 34 that are negatively charged move toward the side of rear substrate 22, and reach rear substrate 22 (see FIG. 2A).

At this time, display medium 12 displays a white color of reflective particles 36 at the side of display substrate 20.

The time T1 required for the above process may be recorded in advance in a memory such as a ROM (not shown)

in control unit 18 as information that indicates the time for voltage application in the initial operation, so that this information is read out upon execution of the operation.

Subsequently, when a voltage having a polarity opposite to the voltage that has been applied between the substrate is applied between the electrodes such that front electrode 40 serves as a positive electrode and rear electrode 46 serves as a negative electrode, mobile particles 34 move toward display substrate 20 to reach display substrate 20. At this time, display medium 12 displays a black color of mobile particles 34 (see FIG. 2B).

Second Exemplary Embodiment

Figure 3:
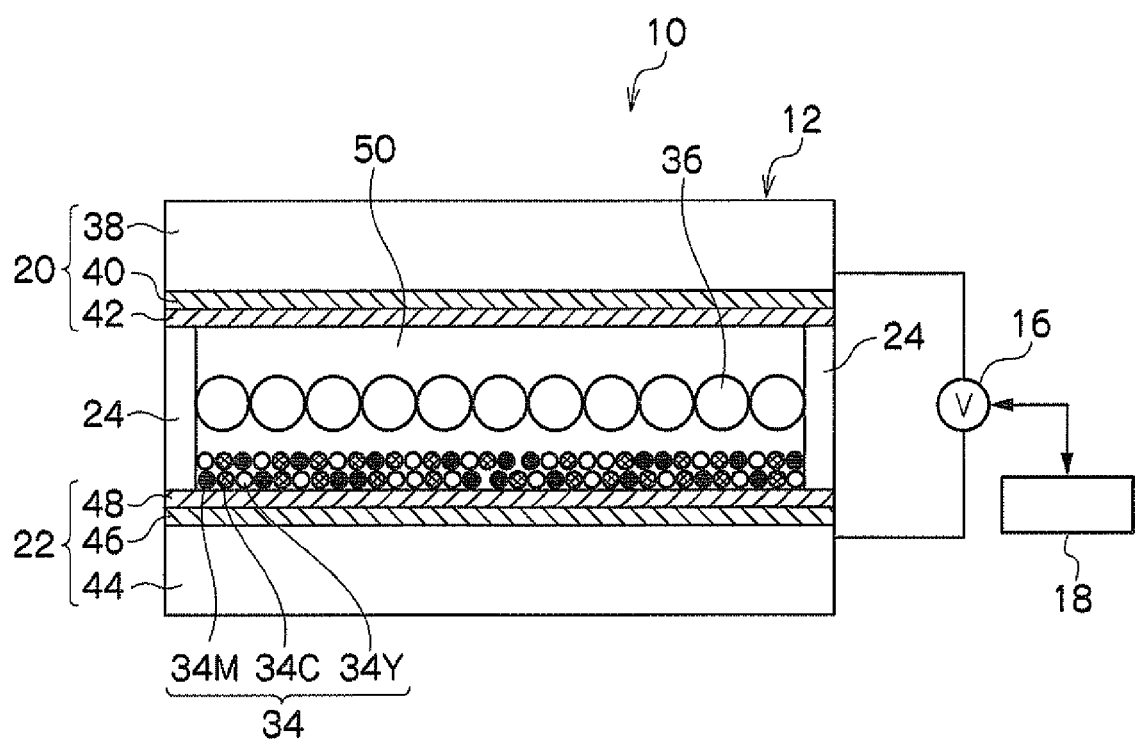
FIG. 3 is a schematic view of a display device according to a second exemplary embodiment of the invention.
Figure 4:
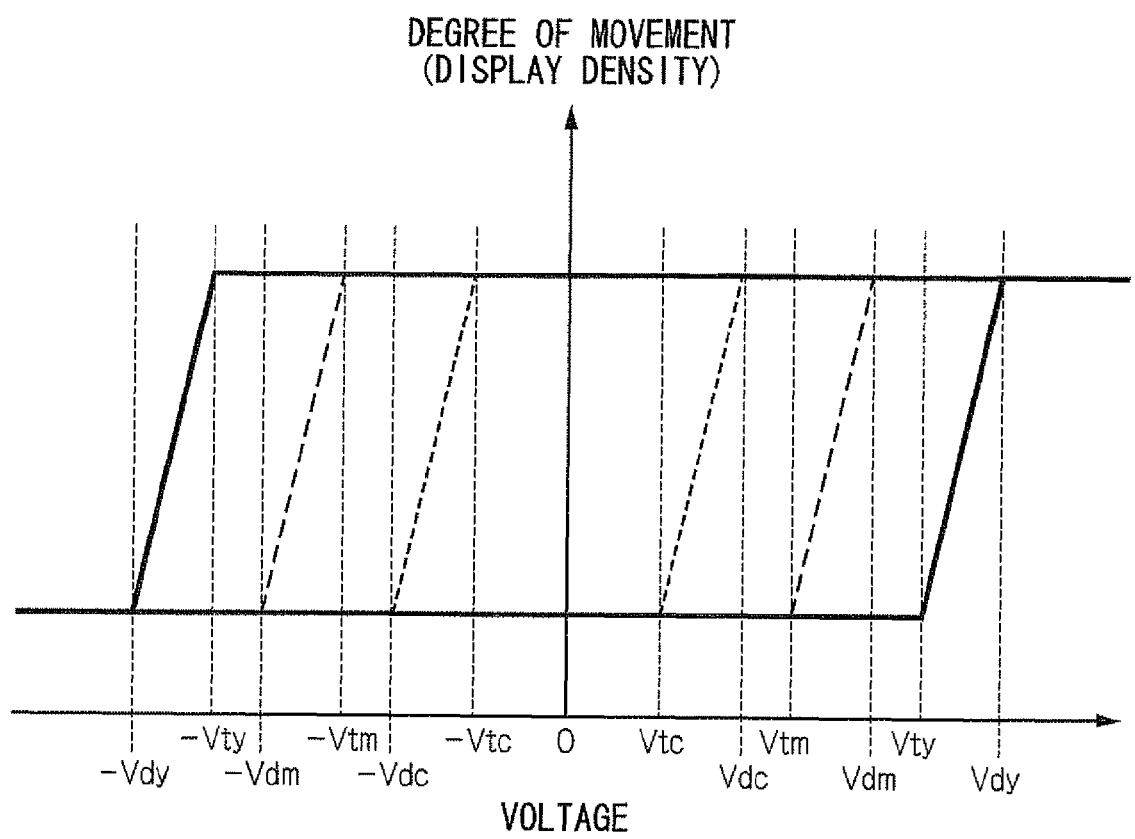
FIG. 4 is a diagram schematically showing the relationship between the voltage and the degree of movement of particles (display density)

In the following, a display device according to the second exemplary embodiment will be described. FIG. 3 is a schematic view of a display device according to the second exemplary embodiment of the invention, FIG. 4 is a diagram schematically showing the relationship between the voltage and the degree of movement of particles (display density), and FIG. 5 is a schematic view showing the relationship between the mode of voltage applied between the substrates of the display medium and the mode of movement of particles.

Display device 10 according to the second exemplary embodiment employs two or more kinds of mobile particles 34, and these two or more kinds of mobile particles 34 are charged to the same polarity. Display device 10 according to the second exemplary embodiment employs particles having a color other than white as mobile particles 34, while the display white particles according to the invention are used as reflective particles 36. It is also possible to employ the white particles for display according to the invention as mobile particles 34 in the display device 10 according to the first exemplary embodiment.

Display device 10 according to this exemplary embodiment includes, as shown in FIG. 3, display medium 12, voltage application unit 16 that applies a voltage to display medium 12, and control unit 18.

Since display device 10 according to this exemplary embodiment has a similar structure to that of display device 10 according to the first exemplary embodiment, the same components are provided with the same indications and detailed explanations thereof are omitted.

Display medium 12 include display substrate 20, rear substrate 22 that is positioned opposite to display substrate 20 with a gap therebetween, spacers 24 that retains these substrates to be positioned via a predetermined space and defines the space between the substrates into multiple cells, mobile particles 34 included in each cell, and reflective particles 36 having an optical reflection characteristics that is different from that of mobile particle 34.

The surfaces of display substrate 20 and rear substrate 22 facing each other are charge-treated as with the case of the first exemplary embodiment, and surface layers 42 and 48 are provided on each of the substrate surfaces.

In this exemplary embodiment, two or more kinds of mobile particles 34 having different colors are dispersed in dispersing medium 50.

In this exemplary embodiment, mobile particles 34 consist of yellow mobile particles 34Y having a yellow color, magenta mobile particles 34M having a magenta color and cyan mobile particles 34C having a cyan color. However, mobile particles 34 are not limited to these three colors.

Mobile particles 34 move between the substrate by electrophoresis, and particles of different colors in response to an electric field at different absolute values of voltage. Namely, yellow mobile particles 34Y, magenta mobile particles 34M and cyan mobile particles 34C move upon application of voltage in a range that is different from each other.

Mobile particles 34 including two or more kinds of particles that move in response to an electric field at different absolute values of voltage can be obtained by preparing particle dispersions each containing particles having different charge amounts, and then mixing these particles dispersions. The charge amount of particles can be adjusted by, for example, changing the amount of materials for mobile particles 34 as described in the first exemplary embodiment, such as a charge control agent or magnetic powder, or changing the type or concentration of the resin that forms the particles.

As mentioned above, display medium 12 according to this embodiment includes three kinds of mobile particles 34 dispersed in dispersing medium 50, i.e., yellow mobile particles 34Y, magenta mobile particles 34M and cyan mobile particles 34C. Mobile particles 34 of different colors move in response to an electric field upon application of a voltage at different absolute values.

In this exemplary embodiment, the absolute value of voltage at which magenta mobile particles 34M start to move is defined as $|Vtm|$, the absolute value of voltage at which cyan mobile particles 34C start to move is defined as $|Vtc|$, and the absolute value of voltage at which yellow mobile particles 34Y start to move is defined as $|Vty|$, respectively. Further, the absolute value of maximum voltage at which substantially all of magenta mobile particles 34M move is defined as $|Vdm|$, the absolute value of maximum voltage at which substantially all of cyan mobile particles 34C move is defined as $|Vdc|$, and the absolute value of maximum voltage at which substantially all of yellow mobile particles 34Y move is defined as $|Vdy|$.

In the following, the relationship among the absolute values of Vtc, −Vtc, Vdc, −Vdc, Vtm, −Vtm, Vdm, −Vdm, Vty, −Vty, Vdy and −Vdy is defined as $|Vtc|<|Vdc|<|Vtm|<|Vdm|<|Vty|<|Vdy|$.

Specifically, as shown in FIG. 4, for example, mobile particles 34 of three kinds are charged to the same polarity and are dispersed in dispersing medium 50, and the range of absolute value of voltage at which cyan mobile particles 34C move $|Vtc \leq Vc \leq Vdc|$ (absolute values between Vtc and Vdc), the range of absolute value of voltage at which magenta mobile particles 34M move $|Vtm \leq Vm \leq Vdm|$ (absolute values between Vtm and Vdm), and the range of absolute value of voltage at which yellow mobile particles 34Y move $|Vty \leq Vy \leq Vdy|$ (absolute values between Vty and Vdy) are set in this order such that these ranges do not overlap each other.

Further, in order to move mobile particles 34 of each color independently from each other, the absolute value of maximum voltage at which substantially all of cyan mobile particles 34C move is set to be less than the range of absolute value of voltage at which magenta mobile particles 34M move $|Vtm \leq Vm \leq Vdm|$ (absolute values between Vtm and Vdm) and the range of absolute value of voltage at which yellow mobile particles 34Y move $|Vty \leq Vy \leq Vdy|$ (absolute values between Vty and Vdy).

Moreover, the absolute value of maximum voltage at which substantially all of magenta mobile particles 34M move is set to be less than the range of absolute value of voltage at which yellow mobile particles 34Y move $|Vty \leq Vy \leq Vdy|$ (absolute values between Vty and Vdy).

Therefore, in this exemplary embodiment, mobile particles 34 of each color can be independently driven by setting the ranges of voltage at which mobile particles 34 of each color move do not overlap each other.

The range of voltage at which mobile particles 34 move is from a voltage at which particles start to move to a voltage at which the display density stops to change (saturated) even when the amount of voltage and application time thereof are increased.

Further, the maximum voltage at which substantially all of mobile particles 34 move is a voltage at which the display density stops to change (saturated) even when the amount of voltage and application time thereof are increased since the start of movement.

The term "substantially all" is used since part of mobile particles 34 may have different characteristics that do not contribute to the display characteristics due to variation in characteristics of mobile particles 34 of each color.

The "display density" refers to a density at which the density per unit of voltage stops to change (saturated), and is determined by measuring an optical density (OD) of color density at the display side, using a reflective densiometer manufactured by X-Rite, Incorporated, while applying a voltage and changing the voltage between the substrates in a direction of increasing the density as measured (increasing or decreasing the voltage for application) even when the amount of voltage and application time thereof are increased.

In display medium 12 according to this exemplary embodiment, when a voltage is applied between display substrate 20 and rear substrate 22 and gradually increased from 0V to exceed +Vtc, display density starts to change due to the movement of cyan mobile particles 34C. When the voltage is further increased to exceed +Vdc, the display density due to the movement of cyan mobile particles 34C stops changing.

When the voltage is further increased to exceed +Vtm, display density starts to change due to the movement of magenta mobile particles 34M. When the voltage is further increased to +Vdm, the display density due to the movement of magenta mobile particles 34M stops changing.

When the voltage is further increased to exceed +Vty, display density starts to change due to the movement of yellow mobile particles 34Y. When the voltage is further increased to +Vdy, display density due to the movement of yellow mobile particles 34Y stops changing.

Conversely, when a voltage of minus polarity is applied between display substrate 20 and rear substrate 22 and the absolute value of the voltage is gradually increased from 0V to exceed −Vtc, display density starts to change due to the movement of cyan mobile particle 34C. When the absolute value of voltage is further increased to −Vdc, the display density due to the movement of cyan mobile particles 34C stops changing.

When the absolute value of voltage is further increased to exceed −Vtm, display density starts to change due to the movement of magenta mobile particles 34M. When the absolute value of voltage is further increased to −Vdm, the display density due to the movement of magenta mobile particles 34M stops changing.

When the absolute value of voltage is further increased to exceed −Vty, display density starts to change due to the movement of yellow mobile particles 34Y. When the absolute value of voltage is further increased to −Vdy, the display density due to the movement of yellow mobile particles 34Y stops changing.

Accordingly, in this exemplary embodiment as shown in FIG. 4, when a voltage in a range of from −Vtc to +Vtc (|Vtc| or less) is applied between display substrate 20 and rear substrate 22, movement of cyan mobile particles 34C, magenta mobile particles 34M and yellow mobile particles 34Y does not occur at such a level that the display density in display medium 12 changes. When a voltage having an absolute value that is more than +Vtc or −Vtc is applied between the substrates, cyan mobile particles 34C (in cyan mobile particles 34C, magenta mobile particles 34M and yellow mobile particles 34Y) start to move at such a level that causes changes in display density in display medium 12, and when a voltage having an absolute value that is more than +Vdc or −Vdc is applied between the substrates, the display density per unit voltage stops changing.

Further, when a voltage in a range of from −Vtm to +Vtm (|Vtm| or less) is applied between display substrate 20 and rear substrate 22, movement of magenta mobile particles 34M and yellow mobile particles 34Y does not occur at such a level that the display density in display medium 12 changes. When a voltage having an absolute value that is more than +Vtm or −Vtm is applied between the substrates, magenta mobile particles 34M (in magenta mobile particles 34M and yellow mobile particles 34Y) start to move at such a level that causes changes in display density in display medium 12, and when a voltage having an absolute value of |Vdm| or more is applied between the substrates, the display density stops changing.

Further, when a voltage in a range of from −Vty to +Vty (|Vty| or less) is applied between display substrate 20 and rear substrate 22, movement of yellow mobile particles 34Y does not occur at such a level that the display density in display medium 12 changes. When a voltage having an absolute value that is more than +Vty or −Vty is applied between the substrates, yellow mobile particles 34Y start to move at such a level that causes changes in display density in display medium 12, and when a voltage having an absolute value of |Vdy| or more is applied between the substrates, the display density stops changing.

Subsequently, the mechanism of how the particles move when an image is displayed in display medium 12 will be described with reference to FIG. 5.

For example, display medium 12 includes yellow mobile particles 34Y, magenta mobile particles 34M and cyan mobile particles 34C as explained with reference to FIG. 4 as mobile particles 34 of plural kinds.

In the following, the voltage to be applied between the substrates that is more than an absolute value at which yellow mobile particles 34Y start moving but not more than a maximum voltage at which substantially all of yellow mobile particles 34Y move is referred to as "voltage L", the voltage to be applied between the substrates that is more than an absolute value at which magenta mobile particles 34M start moving but not more than a maximum voltage at which substantially all of magenta mobile particles 34M move is referred to as "voltage M", and the voltage to be applied between the substrates that is more than an absolute value at which cyan mobile particles 34C start moving but not more than a maximum voltage at which substantially all of cyan mobile particles 34C move is referred to as "voltage S".

When the voltage applied between the substrates is higher at the side of display substrate 20 than the side of rear substrate 22 is applied between the substrates, the above voltages are referred to as "+voltage L", "+voltage M" and "+voltage S", respectively. When the voltage applied between the substrates is higher at the side of rear substrate 22 than the side of display substrate 20, the above voltages are referred to as "−voltage L", "−voltage M" and "−voltage S", respectively.

As shown in FIG. 5, for example, all of magenta mobile particles 34M, cyan mobile particles 34C and yellow mobile particles 34Y are positioned at the side of rear substrate 22 to display a white color at the initial state (see (A)). When +voltage L is applied between display substrate 20 and rear substrate 22 at this initial state, all of magenta mobile particles 34M, cyan mobile particles 34C and yellow mobile particles 34Y move to the side of display substrate 20. These particles remain at the side of display substrate 20 even when the voltage application is stopped at this state, thereby exhibiting a black color formed by subtractive color mixing of magenta, cyan and yellow (see (B)).

Subsequently, when −voltage M is applied between display substrate 20 and rear substrate 22 in the state of (B), magenta mobile particles 34M and cyan mobile particles 34C move to the side of rear substrate 22. As a result, only yellow mobile particles 34Y remain at the side of display substrate 20, thereby exhibiting a yellow color (see (C)).

Further, when +voltage S is applied between display substrate 20 and rear substrate 22 in the state of (C), cyan mobile particles 34C move to the side of display substrate 22. As a result, yellow mobile particles 34Y and cyan mobile particles 34C are positioned at the side of display substrate 20, thereby exhibiting a green color formed by subtractive color mixing of cyan and yellow (see (D)).

When −voltage S is applied between display substrate 20 and rear substrate 22 in the state of (B), cyan mobile particles 34C move to the side of rear substrate 20. As a result, yellow mobile particles 34Y and magenta mobile particles 34M are positioned at the side of display substrate 20, thereby exhibiting a red color formed by subtractive color mixing of yellow and magenta (see (I)).

When +voltage M is applied between display substrate 20 and rear substrate 22 in the state of (A), magenta mobile particles 34M and cyan mobile particles 34C move to the side of display substrate 20. As a result, magenta mobile particles 34M and cyan mobile particles 34C are positioned at the side of display substrate 20, thereby exhibiting a blue color formed by subtractive color mixing of magenta and cyan (see (E)).

When −voltage S is applied between display substrate 20 and rear substrate 22 in the state of (E), cyan mobile particles 34C move to the side of rear substrate 22. As a result, only magenta mobile particles 34M are positioned at the side of display substrate 20, thereby exhibiting a magenta color (see (F)).

When −voltage L is applied between display substrate 20 and rear substrate 22 in the state of (F), magenta mobile particles 34M move to the side of rear substrate 22. As a result, no mobile particles are positioned at the side of display substrate 20, thereby exhibiting a white color of reflective particles 36 (see (G)).

When +voltage S is applied between display substrate 20 and rear substrate 22 in the initial state of (A), cyan mobile particles 34C move to the side of display substrate 20. As a result, cyan mobile particles 34C are positioned at the side of display substrate 20, thereby exhibiting a cyan color (see (H)).

When −voltage L is applied between display substrate 20 and rear substrate 22 in the state of (I), all of mobile particles 34 move to the side of rear substrate 22. As a result, no mobile particles are positioned at the side of display substrate 20, thereby exhibiting a white color of reflective particles 36 (see (G)).

Similarly, when −voltage L is applied between display substrate 20 and rear substrate 22 in the state of (D), all of mobile particles 34 move to the side of rear substrate 22. As a result, no mobile particles are positioned at the side of display substrate 20, thereby exhibiting a white color of reflective particles 36 (see (G)).

In this exemplary embodiment, a voltage corresponding to each kind of mobile particles 34 is applied between the substrates. Therefore, desired particles can be selectively moved in response to an electric field formed by the voltage, migration of particles of other colors in dispersing medium 50 can be suppressed, thereby suppressing mixing of an undesired color. As a result, a color can be displayed while suppressing image degradation of display medium 12.

A vivid color can be displayed as long as mobile particle 34 of different colors move upon application of a voltage having different absolute values, even if the ranges of the voltage overlap each other. However, when the ranges of voltage do not overlap each other, mixing of colors can be more suppressed and a more vivid color display can be realized.

Further, by dispersing mobile particles 34 of cyan, magenta and yellow in dispersing medium 50, colors of cyan, magenta, yellow, blue, red, green and black can be displayed and, for example, a white color can be displayed by using white reflective particle 36, thereby enabling display of a specific color.

As mentioned above, in display device 10 according to this exemplary embodiment, display can be performed by mobile particles 34 that have arrived at display substrate 20 or rear substrate 22.

EXAMPLES

In the following, the invention will be described in further details with reference to the Examples, but the invention is not limited thereto.

Example 1

—Preparation of White Mother Particles A—

300 g of polymethylphenylsilane (trade name: SI-10-10, manufactured by Osaka Gas Chemicals Co., Ltd., refractive index: 1.7, specific gravity: 1.0, structure: (I-1A) where n=60) are pulverized using a supersonic jet mill (trade name: IDS-2, manufactured by Nippon Pneumatic Mfg. Co., Ltd.) and particles having a volume average particle size of 1.5 μm are obtained. These particles are classified, and particles of a polysilane compound having a volume average particle size of 1.0 μm are obtained as white mother particles A.

—Preparation of Reactive Silicone Polymer A—

30 parts by weight of a silicone monomer as a silicone chain component (SILAPLANE FM-0721, trade name, manufactured by Chisso Corporation, volume average molecular weight: 5,000), 5 parts by weight of diethylaminoethyl methacrylate (DEAEMA) as a monomer having a charging group (a component having a charging group) and 65 parts by weight of hydroxymethacrylate as a monomer having no charging group (other copolymerization component) are mixed in 300 parts by weight of isopropyl alcohol (IPA), and 1 part by weight of AIBN (2,2'-azobisisobutyl nitrile) is dissolved therein. The mixture is allowed to polymerize under a nitrogen atmosphere at 60° C. for 24 hours. The obtained product is purified using hexane as a re-precipitation solvent and then dried, thereby obtaining a silicone polymer A.

—Preparation of White Particles 1 (Dispersion 1)—

1 g of white mother particles A and 0.4 g of the silicone polymer A are dissolved and dispersed in 10 g of IPA, and mixed by stirring for 6 hours. This solution is emulsified while gradually adding 20 g of 2CS silicone oil (trade name: KF96, manufactured by Shin-Etsu Chemical Co., Ltd.). Then, the solution is intermittently stirred with an ultrasonic homogenizer for 1 hour while cooling the solution at 30° C. Thereafter, the solution is heated to 50° C. and dried with reduced pressure to evaporate the IPA. White particle dispersion 1 having a volume average particle diameter of 1.0 μm is thus obtained.

The charge polarity of particles in the dispersion is determined by including the dispersion between a pair of electrode substrates and applying a direct current thereto. The direction in which the particles move is evaluated. As a result, the particles are positively charged.

Example 2

—White Mother Particles B—

A mixture of 10 g of polydiphenylsilane (trade name: SI-30-10, manufactured by Osaka Gas Chemicals Co., Ltd., refractive index: 1.74, specific gravity: 1.0, structure: (I-2A)) and 40 g of IPA is pulverized for 60 hours using a ball mil (trade name: IDS-2, manufactured by Nippon Pneumatic Mfg. Co., Ltd.) with 20 g of zirconia beads having a diameter of 2 mm, and particles of a polysilane compound having a volume average particles size of 0.2 μm are obtained as white mother particles B.

—Preparation of White Particles 2 (Dispersion 2)—

1 g of white mother particles B and 0.5 g of silicone polymer A are dissolved and dispersed in 10 g of IPA, and mixed by stirring for 6 hours. This solution is emulsified while gradually adding 20 g of 2CS silicone oil (trade name: KF96, manufactured by Shin-Etsu Chemical Co., Ltd.). Then, the solution is intermittently stirred with an ultrasonic homogenizer for 1 hour while cooling the solution at 30° C. Thereafter, the solution is heated to 50° C. and dried with reduced pressure to evaporate the IPA. White particle dispersion 2 having a volume average particle diameter of 0.2 μm is thus obtained.

The charge polarity of the particles in the dispersion is determined by including the dispersion between a pair of electrode substrates and applying a direct current thereto. The direction in which the particles move is evaluated. As a result, the particles are positively charged.

Comparative Example 1

—Preparation of Dispersion A1—

Dispersion A1 is prepared by mixing the following components and pulverizing the same for 20 hours using a ball mill with zirconia balls having a diameter of 10 mm.

<Composition>

| | |
|---|---|
| Cyclohexyl methacrylate | 61 parts by weight |
| Divinyl methoxy silane | 1 part by weight |
| Titanium oxide 1 (white pigment) (Primary particle size: 0.3 μm, trade name: TIPAQUE CR63, manufactured by Ishihara Sangyo Kaisha, Ltd.) | 35 parts by weight |
| Hollow particles (Primary particle size: 0.3 μm, trade name: SX866(A), manufactured by JSR Corporation) | 3 parts by weight |
| Charge control agent (Trade name: SBT-5-0016, manufactured by Orient Chemical Industries Ltd.) | 1 part by weight |

—Preparation of Calcium Carbonate Dispersion B1—

Calcium carbonate dispersion B1 is prepared by mixing the following components and finely pulverizing the same using a ball mill in a similar manner to the above.

<Composition>

| | |
|---|---|
| Calcium carbonate | 40 parts by weight |
| Water | 60 parts by weight |

—Preparation of Mixed Solution C1—

Mixed solution C1 is prepared by mixing the following components and degassing the same using an ultrasonic machine for 10 minutes, and then stirring the same using an emulsifier.

<Composition>

| | |
|---|---|
| Calcium carbonate dispersion B1 | 8.5 g |
| 20% salt water | 50 g |

—Preparation of Comparative White Particles—

Subsequently, 35 g of dispersion A1, 1 g of ethylene glycol dimethacrylate and 0.35 g of polymerization initiator (AIBN) are thoroughly mixed and degassed for 2 minutes using an ultrasonic machine. The resultant is added to mixed solution C1 as prepared above, and the mixture is emulsified using an emulsifier. The obtained emulsified solution is placed in a bottle and sealed with a silicone cap. The content of the bottle is thoroughly degassed using an injection needle, and the bottle is filled with a nitrogen gas. The content of the bottle is allowed to react at 65° C. for 15 hours at this sate to form particles. The obtained particle powder is dispersed in ion exchange water. Then, the calcium carbonate is decomposed using hydrochloric acid water and filtered. Thereafter, the particle powder is washed with a sufficient amount of distilled water, and unclassified white particles are obtained. The white particles are passed through nylon sieves each having an opening of 10 μm and 15 μm to regulate the particle size. The white particles are dried, and comparative white particles having a volume average particle size of 13 μm and a specific gravity of 1.7 are thus obtained. 2.0 g of comparative white particles are dispersed in 20 g of 2CS silicone oil (trade name: KF96, manufactured by Shin-Etsu Chemical Co., Ltd.), and the comparative white particle dispersion is obtained.

The charge polarity of the particles in the dispersion is determined by including the dispersion between a pair of electrode substrates and applying a direct current thereto. The direction in which the particles move is evaluated. As a result, the particles are negatively charged.

(Evaluation)

Using the white particle dispersions as prepared in the above Examples and Comparative Example, sample devices are prepared by the following method.

Specifically, the white particles dispersion, cyan particle dispersion (below) and a silicone oil (2CS silicone oil, trade name: KF96, manufactured by Shin-Etsu Chemical Co., Ltd.) are mixed in accordance with Table. 1, and the mixture is included in a cell formed between a pair of glass substrates on which an indium tin oxide (ITO) electrode is formed, with a spacer of 50 μm.

—Cyan Particle Dispersion—

65 parts by weight of hydroxyethyl methacrylate, 30 parts by weight of SILAPLANE FM-0721 (trade name, manufactured by Chisso Corporation, volume average molecular weight: 5,000) and 5 parts by weight of methacrylic acid are mixed in 100 parts by weight of isopropyl alcohol, and 0.2 parts by weight of AIBN are dissolved therein as a polymerization initiator. Then, the mixture is allowed to polymerize under a nitrogen atmosphere at 70° C. for 6 hours. The obtained product is purified using hexane as a re-precipitation solvent and dried, thereby obtaining a polymer.

Subsequently, 0.5 g of the above polymer is dissolved in 9 g of isopropyl alcohol. Then, 0.5 g of a cyan pigment (CYANINE BLUE 4973, manufactured by Sanyo Color Works, Ltd.) are added thereto and dispersed for 48 hours using zirconia balls having a diameter of 0.5 mm, thereby obtaining a pigment-containing polymer solution.

To 3 g of this pigment-containing polymer solution, 12 g of 2CS silicone oil (trade name: KF96, manufactured by Shin-Etsu Chemical Co., Ltd.) is gradually dropped and then emulsified while applying ultrasonic waves. Thereafter, the solution is heated to 60° C. and dried with reduced pressure to evaporate the IPA, thereby obtaining particles for display including a polymer and a pigment. The particles for display are allowed to settle using a centrifuge separator and a supernatant liquid is removed. 5 of the above silicone oil are further added thereto and ultrasonic waves are applied, washed and particles are allowed to settle using a centrifuge separator, and the supernatant liquid is removed. Then, 5 of the above silicone oil are further added thereto, and a cyan particle dispersion is thus obtained. The volume average particle size of the cyan particle is 0.2 µm.

The charge polarity of the particles in the dispersion is determined by including the dispersion between a pair of electrode substrates and applying a direct current thereto. The direction in which the particles move is evaluated. As a result, the particles are negatively charged.

—Evaluation Method—

A direct current having a voltage of 10 V is applied to both of the electrodes of the sample device, and then the polarity is reversed to move the particles for display. When a positive voltage is applied to the display side electrode, the cyan particles move to the display side glass substrate to display a cyan color. On the other hand, when a negative voltage is applied to the display side electrode, the cyan particles move to the rear side glass substrate to display a white color. When the white particles are positively charged, the white color is displayed by the movement of the white particles toward the display side glass substrate. When the white particles are not charged, the white color is displayed only by the movement of the cyan particles.

After performing the display of cyan color and white color for 100 times, the white color is displayed by the sample device. At this state, the sample device is left to stand for 5 hours, and the degree of whiteness of the display is evaluated in accordance with the following criteria. The results are shown in Table 1. Further, the degree of sedimentation of the white particles is also evaluated in accordance with the following criteria. The results are shown in Table 1.

—Evaluation of Whiteness—

The degree of whiteness of display is evaluated by measuring a white reflection density using a color reflection densitometer (trade name: X-Rite 404, manufactured by X-Rite Corporation), and then calculating the whiteness by the following formula. The difference between the whiteness as measured at the initial stage and the whiteness as measured after repeating the display process for 100 times is evaluated according to the following criteria.

$$\text{Whiteness (white reflectance ratio)} = 10^{-(white\ reflection\ density)} \times 100\%$$

A: 0 to 10%
B: 11 to 15%
C: 16 to 20%
D: 21% or more

—Degree of Sedimentation of White Particles—

The degree of sedimentation of the white particles are evaluated by placing the dispersion in a colorless, transparent glass sample tube having a volume of 8 ml, and the sample tube is left to stand for 3 hours, 10 hours, 24 hours and 48 hours, respectively. The state of supernatant liquid is observed in accordance with the following criteria.

A: Supernatant liquid is slightly transparent after 48 hours.
B: Supernatant liquid is slightly transparent after 24 hours.
C: Supernatant liquid is slightly transparent after 10 hours.
D: Most particles form a sedimentation and supernatant liquid is transparent after 3 hours.

TABLE 1

|  | White particle dispersion | Cyan particle dispersion | Silicone oil | Whiteness | Sedimentation | Notes |
| --- | --- | --- | --- | --- | --- | --- |
| Example 1 (white particle dispersion 1) | 20 parts by weight | 1 part by weight | 6 parts by weight | B | B |  |
| Example 2 (white particle dispersion 2) | 20 parts by weight | 1 part by weight | 6 parts by weight | A | A |  |
| Comparative Example 1 (comparative white particle dispersion) | 30 parts by weight | 1 part by weight | 6 parts by weight | D | D | * |

* A bluish white color is displayed due to sedimentation of the white particles.

As shown by the above result, Examples 1 and 2 display a white color with a high degree of whiteness while suppressing sedimentation of the white particles, as compared with Comparative Example 1.

All publications, patent applications, and technical standards mentioned in this specification are herein incorporated by reference to the same extent as if each individual publication, patent application, or technical standard was specifically and individually indicated to be incorporated by reference.

What is claimed is:

1. White particles for electrophoresis display comprising at least one of a cyclic polysilane compound having a structure represented by the following Formula (I-2A) or a halogen-substituted compound thereof:

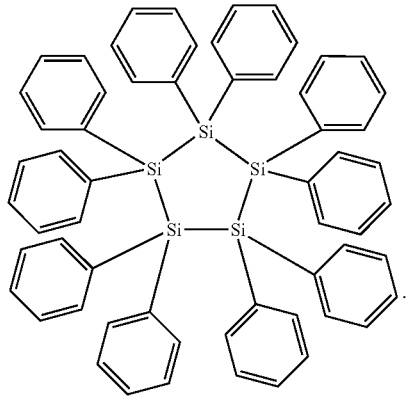

Formula (I-2A)

wherein the white particles have a volume average particle size of from 0.1 μm to 5 μm.

2. A particle dispersion for electrophoresis display comprising the white particles for electrophoresis display according to claim 1 and a dispersing medium for dispersing the white particles for electrophoresis display.

3. White particles for electrophoresis display comprising at least one of a chain or cyclic polysilane compound having a polysilane structure represented by the following Formula (I) or a halogen-substituted compound thereof, and a resin:

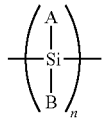

Formula (I)

wherein in Formula (I), A represents a phenyl group, B represents an alkyl group or a phenyl group, and n represents an integer of from 5 to 1000, and the white particles have a volume average particle size of from 0.1 μm to 5 μm.

4. The white particles for electrophoresis display according to claim 3, wherein the resin is a silicone resin.

5. The white particles for electrophoresis display according to claim 3, wherein the amount of the at least one of a chain or cyclic polysilane compound having a polysilane structure represented by Formula (I) or a halogen-substituted compound thereof is from 3 to 99% by weight with respect to the amount of the resin.

6. The white particles for electrophoresis display according to claim 3, wherein the amount of the at least one of a chain or cyclic polysilane compound having a polysilane structure represented by Formula (I) or a halogen-substituted compound thereof is from 10 to 70% by weight with respect to the amount of the resin.

7. A particle dispersion for electrophoresis display comprising the white particles for electrophoresis display according to claim 3 and a dispersing medium for dispersing the white particles for electrophoresis display.

* * * * *